(12) United States Patent
San Miguel

(10) Patent No.: US 7,731,439 B2
(45) Date of Patent: *Jun. 8, 2010

(54) ADVANCING PEN HAVING INDIVIDUALLY CAPPED CARTRIDGES

(76) Inventor: Harry San Miguel, 260 McDonald Ave., San Jose, CA (US) 95116

( * ) Notice: Subject to any disclaimer, the term of this patent is extended or adjusted under 35 U.S.C. 154(b) by 0 days.

This patent is subject to a terminal disclaimer.

(21) Appl. No.: 11/696,100

(22) Filed: Apr. 3, 2007

(65) Prior Publication Data

US 2007/0189833 A1 Aug. 16, 2007

Related U.S. Application Data

(63) Continuation of application No. 10/903,743, filed on Jul. 30, 2004, now Pat. No. 7,226,228.

(51) Int. Cl.
B43K 21/14 (2006.01)
(52) U.S. Cl. .......................................................... 401/57
(58) Field of Classification Search .................. 401/17, 401/29, 32, 55–57
See application file for complete search history.

(56) References Cited

U.S. PATENT DOCUMENTS

| 5,192,270 | A | 3/1993 | Carswell, Jr. |
| 5,989,229 | A | 11/1999 | Chiappetta |
| 6,551,265 | B1 | 4/2003 | Miguel |
| 6,860,666 | B2 | 3/2005 | Chien |
| 7,226,228 | B1 | 6/2007 | San Miguel |

*Primary Examiner*—Tuan N Nguyen
(74) *Attorney, Agent, or Firm*—John Crosby

(57) ABSTRACT

A cartridge for use with an advancing pen, comprising: a cartridge body, the cartridge body containing contents, the cartridge; a seal, the seal retaining the contents within the cartridge body; a cartridge tip, the cartridge tip located substantially within the cartridge body and in contact with the contents and penetrating the seal, the cartridge tip withdrawing the contents to apply the contents to a desired surface; a retaining cap, the retaining cap sealing the cartridge tip and the seal, such that the retaining cap must be removed before the cartridge tip can deliver the contents to the desired surface.

4 Claims, 2 Drawing Sheets

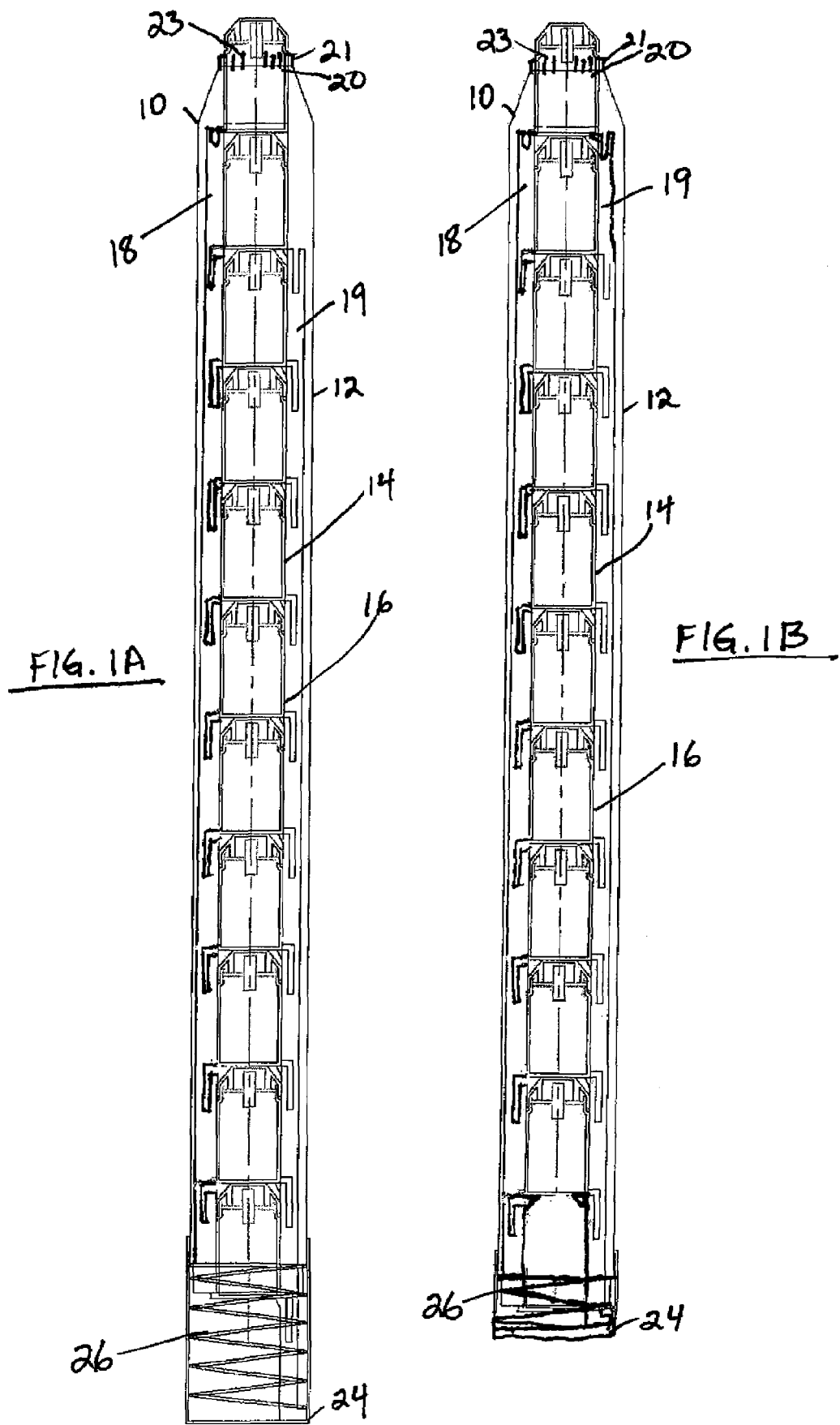

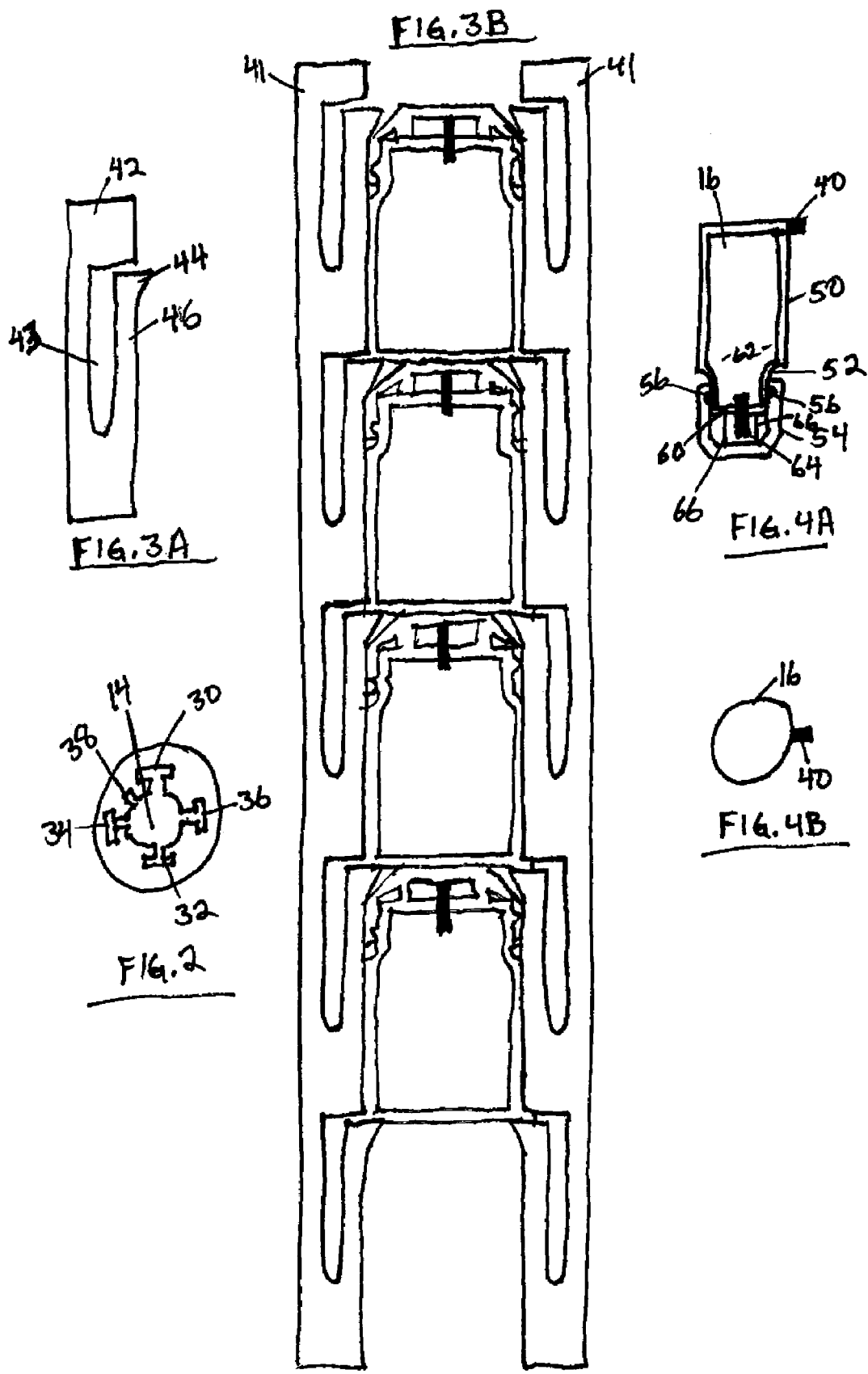

ADVANCING PEN HAVING INDIVIDUALLY CAPPED CARTRIDGES

CROSS-REFERENCE TO RELATED APPLICATIONS

This application is a continuation of co-pending U.S. patent application Ser. No. 10/903,743, filed Jul. 30, 2004, the entirety of which is incorporated by reference herein.

BACKGROUND OF THE INVENTION

1. Field of the Invention

The present invention relates generally to marking pens and applicators. Specifically, the invention relates to an advancing pen having multiple cartridges containing liquid or semisolid material. More specifically, the present invention relates to an advancing pen having multiple cartridges, each cartridge bearing a seal to protect the contents from contamination and loss of moisture.

2. Description of the Prior Art

When medical personnel administer an injection to a patient, draw blood, or perform any intravenous procedure, the area of the skin to be pierced must first be cleansed. The antiseptic used is most often isopropyl alcohol, in part due to its rapid drying characteristic. The rapid drying time can also be a drawback however, as isopropyl alcohol is colorless, and therefore invisible when it has dried, leaving the person performing the procedure in some doubt as to the exact location of the cleansed area. A common procedure among some phlebotomists, for example, is to make a mark on the skin with a pen to identify a desired point of entry after the area is cleansed with isopropyl alcohol. While quick and convenient, this procedure is clearly not optimal, as the pen is very likely to be a source of contamination.

The prior art includes several references for devices that enable the user to either mark or cleanse the site of an intended skin puncture. One such reference for a marking device is the "Hypodermic Syringe and a Method for Marking Injections" by Carswell, U.S. Pat. No. 5,192,270, issued Mar. 9, 1993. This reference discloses a cover for the syringe that has a marking pigment installed at the closed end of the cover. One drawback to this device is that the exposed pigment will not only mark the injection site, but also the user's pocket. Further, there is no provision for an antiseptic agent. A reference that discloses an antiseptic means integral to the syringe unit is the "Needle Cover Assembly having Self-Contained Drug Applicator" of Chiappetta, U.S. Pat. No. 5,989,229, issued Nov. 23, 1999. This device utilizes a drug swab contained in a cover for the needle of the syringe.

U.S. Pat. No. 6,551,265, issued to the inventor of the present invention, discloses an advancing antiseptic marking pen having individual cartridges. However, the disclosed marking pen suffers two drawbacks. First, the barrel of the marking pen includes a slotted aperture running the length of the pen barrel in order to accommodate an advancing mechanism. For medical applications, this aperture is undesirable as foreign debris and other contaminants can enter the inside of the marking pen through the aperture. Also, the individual marking cartridges disclosed are not individually sealed, also posing a sanitary risk in medical applications, as well as shortening the useful life of the fluids contained in the individual cartridges as they can prematurely lose moisture.

There is no reference in the prior art that discloses a device that enables the user to both cleanse and to mark the intended site of an injection or other sub-dermal procedure. This means that the medical technician must use more than one instrument for each such procedure.

Accordingly, it is an object of the present invention to provide a device suitable for sterile applications that can both apply an antiseptic while simultaneously marking a site on a patient's skin. It is a further object of the present invention to provide a device that accomplishes sterile marking. It is a still further object of the present invention to provide a device that is quick and easy to use.

SUMMARY

The present invention provides a cartridge for use with the advancing pen described above. A cartridge comprises a cartridge body containing liquid or semisolid contents, a seal that retains the contents within the cartridge body, a cartridge tip located substantially within the cartridge body and in contact with the contents and penetrating the seal. The applicator tip withdraws the contents through a wicking action to apply the marking contents to a desired surface. The cartridge tip and seal are covered by a retaining cap. When the cartridge is advanced through the advancing pen to partially protrude through the opening, the retaining cap is removed before the cartridge tip can deliver the marking contents to the desired surface. In yet another embodiment, the cartridge can contain solid material such as pills or powder.

Many other features and advantages of the present invention will be realized by one skilled in the art upon reading the following detailed description, when considered in connection with the accompanying drawings, in which:

BRIEF DESCRIPTION OF THE DRAWINGS

FIGS. 1A and 1B illustrates a cutaway view of the advancing pen and cartridges of the present invention;

FIG. 2 illustrates the profile of the inner chamber of the advancing pen;

FIGS. 3A and 3B illustrate the retaining rack and movable rack placed in the inner chamber of the advancing pen of the present invention;

FIGS. 4A and 4B illustrate a cross section view and plan view, respectively, of the cartridge of the present invention.

DETAILED DESCRIPTION

Directing attention to FIGS. 1A and 1B, there is shown advancing pen 10 of the present invention. Advancing pen 10 comprises barrel 12 formed around inner chamber 14. Inner chamber 14 receives a plurality of cartridges 16, which are held in place by a plurality of retaining racks 18 and similarly-shaped movable racks 19. The cartridges 16 are driven through opening 20 at the head of barrel 12 by rear driving cap 24, which engages spring member 26 against the movable racks to advance cartridges 16 within retaining racks 18. The leading cartridge is retained midway through opening 20. FIG. 1A shows the orientation of cartridges 16 in their initial state, before rear driving cap 24 is engaged to advance the cartridges forward. FIG. 1B shows the orientation of cartridges 16 (less one cartridge that was discharged when rear driving cap 24 was depressed to engage movable racks 19, thus driving cartridges 16 forward by the distance of one cartridge. In an embodiment, the forward-most cartridge, which is partially exposed through opening 20, is retained by retainer member 21, which can be implemented as a substantially circular ring that attaches to opening 20 and has a plurality of fingers 23 which exert pressure inward toward the center of the exposed cartridge, thus keeping the forward-most cartridge and preventing it from slipping out of opening 20 until movable rack 19 is again engaged.

FIG. 2 illustrates a cross sectional view along the longitudinal axis of inner chamber 14. Channels 30, 32 receive retaining racks 18 and channels 34, 36 receive the movable racks. Channels 30, 32, 34 and 36 are similarly dimensioned to as retaining racks 18 and movable racks 19 are similarly dimensioned. However, retaining racks 18 are secured within channels 30, 32, while movable racks 19 are allowed to slide back and forth within channels 34, 36. In an embodiment, a smaller alignment channel 38 is also included to receive an alignment pin 40 on cartridge 16. Alignment pin 40, when inserted in alignment channel 38, keeps cartridge 16 from rotating within inner chamber 14.

FIGS. 3A and 3B illustrate the profile of retaining rack 18 as well as retaining rack 18 and movable rack 19. Retaining rack 18 and movable rack 19 can be conceptually visualized as a plurality of rack pins formed into an integral unit 41 (FIG. 3A). Each rack pin 42 comprises engaging member 44, which protrudes inwardly into inner chamber 16 to engage cartridge 16 at shoulder 50. Rack pin 42 is formed around a hollow area 43 that allows engaging member 44 and arm 46 to flex outward from the longitudinal axis of inner chamber 14 when rear driving cap 24 is depressed, thus allowing cartridge 16 to advance along retaining racks 18. Movable racks 19 are secured to spring member 26 such that when rear driving cap 24 is depressed, movable racks 19 drive the plurality of cartridges 16 forward by the distance of one cartridge. When rear driving cap 24 is released, movable racks 19 return to their original position. In an embodiment, movable racks 19 exceed retaining racks 18 by the length of one cartridge. In an embodiment, rear driving cap 24 and spring member 26 can be removed from advancing pen 10, so that additional cartridges 16 can be reloaded into the rear of advancing pen 10.

FIG. 4A illustrates an elevation view of cartridge 16. In an embodiment, cartridge 16 includes alignment pin 40, more clearly illustrated in FIG. 4B. Cartridge 16 comprises a substantially cylindrical body 50. In an embodiment, cylindrical body 50 comprises a taper at location 52 that is sufficiently dimensioned to receive cartridge cap 54. In an embodiment, cartridge cap 54 screws onto cartridge 16 by engaging thread 56 on cartridge 16, but other attachment mechanisms can be used, such as incorporating a lip rather than a thread on cartridge 16, or simply using a pressure fit between cartridge cap 54 and cartridge 16. In an embodiment, cartridge cap 54 comprises retaining members 58, that engage seal 60 on cartridge 16. In an embodiment, seal 60 is a circular member having an aperture sufficiently dimensioned to allow cartridge tip 64 to protrude from cartridge 16. Seal 60 provides an added layer of moisture barrier and sealant to protect contents 62 within cartridge 16 from loss of moisture and/or contamination. Cartridge tip 64 is shielded by seal cartridge cap 54 until cartridge cap 54 is removed. In an embodiment, cartridge tip 64 comprises a material such as felt, or other suitable material, that is able to wick contents 62 and apply them to a desired surface. In an embodiment, cartridge cap 54 includes engaging member 66, which is a circular member that engages seal 60 with even pressure until cartridge cap 54 is removed.

Contents 62 can embody a wide variety of fluids and semi-solid materials. The present invention is particularly useful as an antiseptic marking pen for medical applications, allowing a healthcare worker to sterilize and mark an area of skin for medical procedures. Due to the closed structure of advancing pen 10 and the use of cartridge cap 54, contents 62 can be maintained in a sterile environment and protected from loss of moisture. Advancing pen 10 can be used in a wide variety of non-medical applications, such as a traditional marking pen. The advantage of the present invention again is in the sealed, individual cartridges, which can contain similar materials or similar colors, or in different embodiments, contents 62 can vary between individual cartridges.

The above disclosure is not intended to be limiting. While advancing pen 10 is described in terms of being a marking pen, it is capable of delivering a wide variety of liquid and semisolid materials in non-marking applications, such as adhesives, cosmetics, and cleansing materials such as alcohol, liquid detergent, bleach, and the like. Advancing pen 10 is especially useful in medical applications for applying medical adhesives, sterilizing agents, medicines applied topically, and other materials useful in medical applications.

In an alternative embodiment, advancing pen 10 can be used to dispense solid materials. In this embodiment, cartridge 16 does not include a cartridge tip, but still incorporates cartridge cap 54 to retain solid materials within cartridge 16. This embodiment of the present invention is especially useful in that advancing pen 10 can be used as a medication dispenser, with each cartridge 16 containing a measured dose of medicine, nutritional supplements or vitamins, such as a pill, combination of pills, or substance in powdered form, to be taken at certain intervals.

Those skilled in the art will readily recognize that numerous modifications and alterations can be made to the various embodiments of the present invention without departing from the spirit thereof.

What is claimed is:

1. A cartridge for use with an advancing pen, comprising:
a cartridge body, the cartridge body containing contents;
a seal, the seal retaining the contents within the cartridge body;
a cartridge tip, the cartridge tip located substantially within the cartridge body and in contact with the contents and penetrating the seal, the cartridge tip withdrawing the contents to apply the contents to a desired surface;
a retaining cap, the retaining cap sealing the cartridge tip and the seal, such that the retaining cap must be removed before the cartridge tip can deliver the contents to the desired surface; and
an alignment tab, the alignment tab protruding radially from the cartridge body, and extending along the length of the cartridge body, said alignment tab serving to prevent rotation of said cartridge body within a dispensing pen by fitting into a longitudinal slot located on an interior surface of the dispensing pen.

2. The cartridge of claim 1, wherein the cartridge body is substantially cylindrical in shape.

3. The cartridge of claim 1, wherein the retaining cap fits onto the cartridge body utilizing a pressure fit.

4. The cartridge of claim 1, wherein the contents are antiseptic.

* * * * *